(12) United States Patent
Nishijima et al.

(10) Patent No.: US 9,410,493 B2
(45) Date of Patent: Aug. 9, 2016

(54) CONTROL UNIT FOR INTERNAL-COMBUSTION ENGINE

(75) Inventors: Hiroki Nishijima, Suntou-gun (JP); Tatsuhiro Hashida, Susono (JP)

(73) Assignee: TOYOTA JIDOSHA KABUSHIKI KAISHA, Toyota-shi (JP)

( * ) Notice: Subject to any disclaimer, the term of this patent is extended or adjusted under 35 U.S.C. 154(b) by 403 days.

(21) Appl. No.: 14/236,549

(22) PCT Filed: Aug. 4, 2011

(86) PCT No.: PCT/JP2011/067858
§ 371 (c)(1),
(2), (4) Date: Jan. 31, 2014

(87) PCT Pub. No.: WO2013/018224
PCT Pub. Date: Feb. 7, 2013

(65) Prior Publication Data
US 2014/0165979 A1    Jun. 19, 2014

(51) Int. Cl.
*F02M 51/00* (2006.01)
*F02D 41/00* (2006.01)
*F01N 9/00* (2006.01)
*F01N 11/00* (2006.01)
(Continued)

(52) U.S. Cl.
CPC ............ *F02D 41/0047* (2013.01); *F01N 9/002* (2013.01); *F01N 11/00* (2013.01); *F02D 41/1466* (2013.01); *F02D 41/1467* (2013.01); *F02D 41/22* (2013.01); *G01N 15/0606* (2013.01); *G01N 15/0656* (2013.01);
(Continued)

(58) Field of Classification Search
CPC .... F01N 11/00; F02N 41/1466; F02N 41/222

USPC ............................. 123/478, 479; 60/274, 285
See application file for complete search history.

(56) References Cited

U.S. PATENT DOCUMENTS 9,151,204 B2 * 10/2015 Hashida .................. F01N 11/00
2010/0206167 A1 * 8/2010 Okayama ............. G01N 27/226
96/19
(Continued)

FOREIGN PATENT DOCUMENTS

JP    2009 144577    7/2009
JP    2010 144695    7/2010
(Continued)

OTHER PUBLICATIONS

International Search Report Issued Nov. 15, 2011 in PCT/JP11/067858 Filed Aug. 4, 2011.

*Primary Examiner* — John Kwon
(74) *Attorney, Agent, or Firm* — Oblon, McClelland, Maier & Neustadt, L.L.P.

(57) ABSTRACT

According to the invention, a particulate matter sensor is installed in an exhaust passage of an internal-combustion engine. A control unit for this internal-combustion engine detects a particulate amount in an exhaust gas through the exhaust passage in response to an output from the particulate matter sensor. Further, the control unit for the internal-combustion engine forms a particulate layer on electrode surfaces of the particulate matter sensor by applying a particulate capturing voltage between the electrodes during a first period. Further, the control unit maintains the formed particulate layer during a second period. It is noted here that the phrase "maintain the formed particulate layer" includes the meanings "maintaining the formed particulate layer as it is" and "inhibiting control to remove the particulate layer".

9 Claims, 5 Drawing Sheets

(51) Int. Cl.
*F02D 41/14* (2006.01)
*F02D 41/22* (2006.01)
*G01N 15/06* (2006.01)
*F02D 41/02* (2006.01)
*F02D 41/06* (2006.01)
*F02D 41/18* (2006.01)
*G01N 15/00* (2006.01)

(52) U.S. Cl.
CPC ......... *F01N2550/04* (2013.01); *F01N 2560/05* (2013.01); *F01N 2560/20* (2013.01); *F02D 41/029* (2013.01); *F02D 41/06* (2013.01); *F02D 41/1494* (2013.01); *F02D 41/18* (2013.01); *G01N 2015/0046* (2013.01); *Y02T 10/40* (2013.01); *Y02T 10/47* (2013.01)

(56) References Cited

U.S. PATENT DOCUMENTS

| 2011/0283773 | A1* | 11/2011 | Suzuki | G01K 7/16 73/25.05 |
| 2011/0320171 | A1* | 12/2011 | Okayama | B01D 46/0086 702/183 |
| 2012/0125081 | A1* | 5/2012 | Yadav | F01N 11/00 73/23.33 |

FOREIGN PATENT DOCUMENTS

| JP | 2011-21479 A | 2/2011 |
| JP | 2011 089430 | 5/2011 |

\* cited by examiner

CONTROL UNIT FOR INTERNAL-COMBUSTION ENGINE

TECHNICAL FIELD

The present invention relates to a control unit for internal-combustion engine. More specifically, the invention relates to a control unit for internal-combustion engine that includes a particulate matter sensor installed in an exhaust passage of the internal-combustion engine and detecting an amount of particulate matter in an exhaust gas.

BACKGROUND ART

In a system disclosed in Patent Document 1, for example, a DPF (Diesel Particulate Filter) for capturing particulate matter in an exhaust gas (hereinafter, also referred to as "PM") is disposed in the exhaust passage of the internal-combustion engine. Disposed downstream of the DPF is a PM sensor for detecting the amount of PM which was not captured by the DPF and allowed to pass therethrough.

The PM sensor of Patent Document 1 includes an insulating layer allowing the adhesion of PM and electrodes disposed on the insulating layer and spaced from each other. When the PM sensor is exposed to the exhaust gas so that the PM in the exhaust gas is deposited between the electrodes, conductivity between the electrodes varies according to the deposition amount of PM and hence, inter-electrode resistance varies. According to Patent Document 1, the PM amount in the exhaust gas related with the amount of inter-electrode PM deposition is detected by detecting the resistance value of the PM sensor. Hence, a malfunction of DPF or the like is detected based on the resistance value of the PM sensor.

By the way, when the amount of inter-electrode PM deposition exceeds a given value, the inter-electrode resistance does not vary any more, which disables the subsequent output of a value corresponding to a PM deposition amount. According to a technique of Patent Document 1, on the other hand, at a point in time when the amount of inter-electrode PM deposition is increased to some degree, PM reset is performed by heating an element part of the PM sensor by means of a built-in heater for a predetermined length of time so as to combustively remove the deposited PM.

PRIOR ART DOCUMENT

Patent Documents

Patent Document 1: Japanese Patent Application Publication No. 2009-144577 (JP 2009-144577 A)

SUMMARY OF THE INVENTION

Problem to be Solved by the Invention

By the way, the exhaust gas contains Ash (soot) derived from a lubricant and metal compounds derived from oxidation of a catalyst as well as the PM including soot (soot-like substances such as carbon) and SOF (soluble organic fraction) which derive from combustion in the internal-combustion engine. If these Ash and metal compounds become adhered to the electrodes of the PM sensor, the sensor output may sometimes vary. Accordingly, the adhesion of Ash and the metal compounds (hereinafter, also referred to as "poisonous substances" including Ash and the metal compounds) can possibly induce an event that malfunction detection of DPF and the like based on the sensor output is decreased in accuracy.

In addition, Ash and the metal compounds have higher combustion temperatures than the PM so that it is difficult to combustively remove these substances by a process of overheating the element part using the heater built in the PM sensor. If the poisonous substances directly adhere between the electrodes, the adhered poisonous substances remain on the electrodes even after the combustion removal of the PM. With repeated PM resets, the amount of adhered poisonous substances progressively increase, further lowering the accuracies of the PM amount detection by the PM sensor and the malfunction detection of DPF based on the above detection result.

With an aim to address the above problem, the invention provides a control unit for internal-combustion engine that is so improved as to suppress the adhesion of Ash and metal compounds contained in the exhaust gas to the electrodes and to maintain high accuracies of the PM amount measurement.

Means for Solving the Problem

According to the invention for achieving the above object, a particulate matter sensor is installed in an exhaust passage of the internal-combustion engine. According to the invention, a control unit for internal-combustion engine includes: detecting means for detecting a particulate amount in an exhaust gas through an exhaust passage in response to an output from the particulate matter sensor; forming means for forming a particulate layer on surfaces of electrodes of the particulate matter sensor by applying a particulate capturing voltage between the electrodes during a first period; and maintaining means for maintaining, during a second period, the state where the particulate layer is formed. It is noted here that the "maintaining means" includes means for maintaining the state of the formed particulate layer as it is and means for inhibiting the control to remove the particulate layer.

The control unit for internal-combustion engine according to the invention is applicable to a structure wherein a particulate capturing filter for capturing the particulate matter in the exhaust gas is disposed in the exhaust passage at place upstream of the particulate matter sensor. In this case, the above "first period" may be defined as a period between the completion of malfunction detection control to determine whether a malfunction of the particulate capturing filter exists or not and a reference output reached by the output of the particulate matter sensor, and the above "second period" may be defined as a period between the reference output reached by the output of the particulate matter sensor and the shutdown of the internal-combustion engine. In this case, the maintaining means may maintain the particulate layer by stopping the application of the capturing voltage.

The control unit for internal-combustion engine according to the invention may further include means for combustively removing the particulate matter deposited on an element part by raising the temperature of the element part. In this case, the control unit for internal-combustion engine may further include temperature control means for controlling the element part to be at a predetermined temperature lower than a temperature for combustive removal of the particulate matter but high enough to suppress the deposition of the particulate matter on the element part during a period between the voltage application by the forming means continued till an output of the particulate matter sensor reaches the reference output and the shutdown of the internal-combustion engine.

The control unit for internal-combustion engine according to the invention is applicable to the structure wherein the particulate capturing filter for capturing the particulate matter in the exhaust gas is disposed in the exhaust passage at place upstream of the particulate matter sensor. In this case, "the first period" may include at least a period up to the start of filter regeneration control to remove the particulate matter deposited in the particulate capturing filter, and "the second period" may include at least a period between the prediction of the start of the filter regeneration control and the completion of the filter regeneration control. Further, the control unit for internal-combustion engine may include removing means for combustively removing the particulate matter deposited on an element part by raising the temperature of the element part formed with the electrodes of the particulate matter sensor, and have the structure wherein the maintaining means maintains the particulate layer by inhibiting the combustive removal of the particulate matter deposited on the element part.

In this case, "the first period" may include a period between the prediction of the start of the filter regeneration control and the start of the filter regeneration control, or "the second period" may further include a period between the completion of the filter regeneration control and a reference deposition amount exceeded by the particulate matter deposited in the particulate capturing filter.

According to the invention, the control unit for internal-combustion engine may further include: means for estimating a particulate amount in the exhaust gas emitted from the internal-combustion engine; and inhibiting means for inhibiting the maintenance of the particulate layer by the above-described maintaining means in a case where the estimated particulate amount is smaller than a reference emission volume.

Effect of the Invention

According to the invention, the particulate layer is formed on the electrode surface of the particulate matter sensor during the first period, and this particulate layer is maintained during the second period. Herewith, the electrode surface of the particulate matter sensor is protected during the second period so that the direct adhesion of the poisonous substances in the exhaust gas onto the electrode surface can be suppressed. Even if the poisonous substances adhere onto the particulate layer on the electrode surface during the second period, the poisonous substances can be scattered in the combustion removal of the particulate layer adhered to the electrodes. Thus, the increase of the amount of poisonous substances adhered onto the electrodes can be suppressed. Herewith, time degradation of the particulate matter sensor, such as output variations, can be avoided.

In particular, the state where the particulate matter deposited on the element part is combustively removed is established before the start of malfunction detection control for the particulate capturing filter, for example. Therefore, if the state with the particulate matter removed from the element part is allowed to stand as it is after the completion of the malfunction detection control for the particulate capturing filter, the poisonous substances in the exhaust gas can possibly adhere directly to the electrodes together with the particulate matter. In this regard, however, if the particulate layer is formed by applying the particulate capturing voltage during the "first period" between the completion of the malfunction detection control for the particulate capturing filter and the reference output exceeded by the output of the particulate matter sensor and then, is maintained till the shutdown of the internal-combustion engine, as taught by the invention, the electrodes can be protected by the particulate layer during a period following the completion of the malfunction detection control for the particulate capturing filter, in which the output from the particulate matter sensor is not used. Therefore, the increase of the amount of poisonous substances deposited on the electrodes can be suppressed.

It is noted here that the particulate layer has some degree of water repellent effect. Therefore, if the control unit is adapted to maintain the particulate layer during the period up to the shutdown of the internal-combustion engine, the particulate matter sensor can be more quickly raised in temperature at the subsequent start-up of the internal-combustion engine, while preventing element fracture due to exposure to water.

If the control unit has means for controlling the element part to be at the predetermined temperature to suppress the deposition of the particulate matter after the end of applying the capturing voltage to the particulate matter sensor, the deposition of the poisonous substances on the element part can be more assuredly prevented. At the subsequent start-up of the internal-combustion engine, the particulate matter sensor can be made ready for the particulate amount detection by more promptly raising the temperature of the particulate matter sensor.

Particularly during the period of filter regeneration control to remove the particulate matter deposited in the particulate capturing filter, for example, the amount of the particulate matter and poisonous substances allowed to pass through the particulate capturing filter and emitted to the downstream tends to increase. In this regard, however, if the particulate layer is formed during the period before the start of filter regeneration control and the particulate layer is maintained during the period between the prediction of the start of filter regeneration control and the completion of the control, as taught by the invention, the state where the electrodes are protected with the particulate layer is established before entering an operational region where the poisonous substances are apt to increase. Thus, the electrodes can be protected with the particulate layer during the period when the poisonous substances increase. Herewith, the direct adhesion of the poisonous substances to the electrodes can be prevented and hence, the degradation of the particulate matter sensor can be suppressed.

After the filter regeneration control, the particulate matter and poisonous substances emitted to the downstream of the particulate matter sensor are apt to increase till a certain amount of particulate matter deposits in the particulate capturing filter. In this regard, however, if the particulate layer is also maintained during the period between the completion of the filter regeneration control and the reference deposition amount exceeded by the particulate matter deposited in the particulate capturing filter, the direct adhesion of the poisonous substances to the electrodes can be suppressed under an environment where a large amount of poisonous substances exist.

According to the invention, in the structure where the maintenance of particulate layer is inhibited when the estimated particulate amount in the exhaust gas emitted from the internal-combustion engine is lower than the reference emission volume, the particulate matter sensor can be operated with higher accuracies in a region where the particulate amount is particularly low. Herewith, the particulate matter sensor can be operated effectively while suppressing the degradation thereof.

MODES FOR CARRYING OUT THE INVENTION

Figure 1:
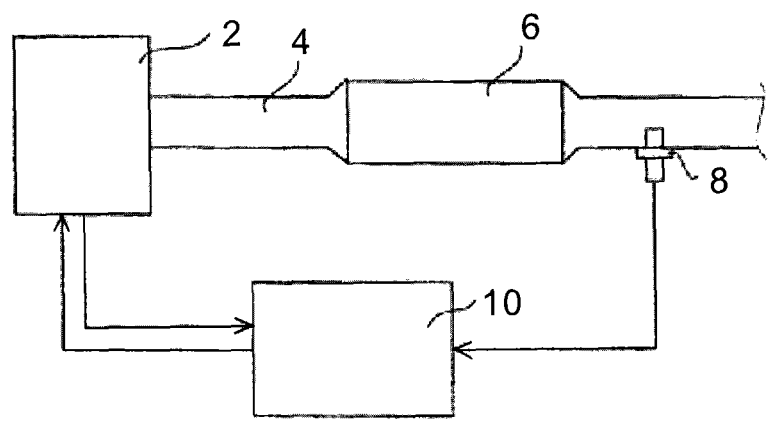
FIG. 1 is a schematic diagram illustrating an overall structure of a system according to a first embodiment of the invention.

The embodiment of the invention will be described as below with reference to the accompanying drawings. Identical or equivalent elements in the figures will be referred to by like reference numerals, description of which will be simplified or dispensed with.

First Embodiment

Structure of System According to the Embodiment

FIG. 1 is a diagram for illustrating an overall structure of a system according to an embodiment of the invention. In the system shown in FIG. 1, a DPF 6 (Diesel Particulate Filter) is installed in an exhaust passage 4 of an internal-combustion engine 2. The DPF 6 is a filter for capturing a particulate matter (PM) contained in an exhaust gas. A PM sensor 8 (particulate matter sensor) is installed in the exhaust passage 4 at place downstream of the DPF 6. The PM sensor 8 is used for detecting the PM amount in the exhaust gas passed through the DPF 6.

This system includes a control unit 10. The PM sensor 8 and a variety of sensors are connected to an input side of the control unit 10. Various actuators of the internal-combustion engine 2 are connected to an output side of the control unit 10. The control unit 10 provides various controls related to the internal-combustion engine 2 by executing predetermined programs based on input information from the various sensors and operating the various actuators.

Figure 2:
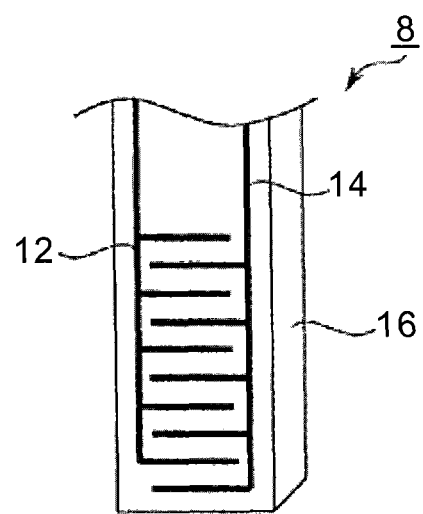
FIG. 2 is a schematic diagram illustrating a configuration of an element part of a PM sensor according to the first embodiment of the invention.

FIG. 2 is a schematic diagram showing in enlarged dimension an element part of the PM sensor 8 according to the first embodiment of the invention. As shown in FIG. 2, the element part of the PM sensor 8 includes a pair of electrodes 12, 14 mounted on a surface thereof. The pair of electrodes 12, 14 are arranged a given distance apart from each other so as to be out of contact with each other. Further, the electrodes 12, 14 have a comb-shaped part, respectively and are so arranged as to be interdigitated with each other at the comb-shaped parts thereof. The electrodes 12, 14 are in contact with an insulating layer 16 formed thereunder. The insulating layer 16 has a function to allow the PM to adhere thereto. An unillustrated heater is embedded in the insulating layer 16 under the electrodes 12, 14.

The electrode 12 and the electrode 14 are connected to a power supply (not shown) via a supply circuit and the like, respectively. Herewith, a predetermined voltage can be applied between the electrode 12 and the electrode 14. The heater is connected to a power supply (not shown) via a supply circuit and the like so that the element part is heated by supplying a predetermined electric power to the heater. The supply circuit and the like are connected to and controlled by the control unit 10.

Summary of Control According to the Embodiment

The control provided by the control unit 10 according to the embodiment includes: detection of PM amount in exhaust gas and malfunction decision on DPF 6 based on the detection result; regeneration of DPF 6; and resetting of PM sensor 8.

(1) Detection of PM Emission Volume

In the detection of PM emission volume, the control unit 10 applies a "capturing voltage" as voltage to capture the particulate matter between the electrodes 12, 14. When the capturing voltage is applied between the electrodes 12, 14, the PM in the exhaust gas is captured and deposited between the electrodes 12, 14. With the increase in the PM deposited between the electrodes 12, 14, conductive areas between the electrodes 12, 14 increase so as to reduce resistance between the electrodes 12, 14. In the following embodiments, a current value is detected as a sensor output of the PM sensor 8. Namely, the output of the PM sensor 8 increases with the increase in the amount of PM deposited between the electrodes 12, 14. Further, the amount of PM deposited between the electrodes 12, 14 increases or decreases in conjunction with the PM amount in the exhaust gas, namely the amount of PM passed through the DPF 6 and emitted to the downstream.

In the first embodiment, therefore, a relation between the sensor output and the PM emission volume is previously determined. Based on this relation, the PM emission volume in the exhaust gas is detected according the output from the PM sensor 8. Hereinafter, a state where the sensor output is detected while applying the capturing voltage will be also referred to as "PM detection mode". It is assumed that the element part is maintained at temperature equal to or less than 300° C. in the PM detection mode.

(2) DPF Malfunction Decision (Malfunction Decision Control)

A malfunction of the DPF 6 may result in an event that the PM is allowed to pass through the DPF 6 and emitted to the atmosphere. Therefore, the control unit 10 periodically performs control to determine whether any malfunction of the DPF 6 exists or not. Specifically, the control unit 10 estimates the amount of PM contained in the exhaust gas rearward (downstream) of the DPF 6 according to a model. The control unit 10 decides on the presence of some malfunction of the DPF 6 by comparing the estimated amount (hereinafter, also referred to as "estimated PM emission volume") and the PM emission volume corresponding to the output of the PM sensor 8. That is, the control unit determines that the DPF 6 is broken down if a detection value of the PM emission volume based on the output from the PM sensor 8 is greater than the estimated PM emission volume. It is noted that the estimated PM emission volume used for this decision is a value given by adding an allowable margin to the estimated emission volume of PM contained in the exhaust gas downstream of the DPF 6, the estimated emission volume calculated based on the model.

(3) Regeneration of DPF 6 (Filter Regeneration Control)

If the DPF 6 continues to capture the PM in the exhaust gas, the amount of PM deposited in the DPF 6 (also referred to as "PM deposition amount") will eventually reaches a limit so that the DPF 6 cannot capture the PM any more. In order to avoid such an event, a processing of recovering the DPF 6 by combustively removing the PM is performed when the PM deposition amount reaches some level.

Specifically, in the regeneration process of DPF 6, the control unit 10 performs control to raise exhaust gas temperature according to predetermined control programs such as a control to re-inject a fuel after fuel injection, a control to delay injection timing, and the like. Thus, the PM deposited in the DPF 6 is removed by combustion. Much of the PM deposited in the DPF 6 is removed by performing such a combustion removal of PM for a given length of time and the regeneration of DPF 6 is completed.

The control unit 10 estimates the deposition amount of PM in the DPF 6 by estimating the PM amount in the exhaust gas emitted from the internal-combustion engine 2 according to a model or the like. The control unit determines a time when the estimated amount (hereinafter, also referred to as "estimated deposition amount of PM") reaches a predetermined amount as a timing of the regeneration of DPF 6, and performs the above regeneration process.

(4) PM Reset (Control to Remove Particulate Matter by Combustion)

The output from the PM sensor 8 is an output varying according to the amount of PM deposited on the element part. Therefore, a predetermined time to start the malfunction decision on DPF 6 or a predetermined time following the regeneration of DPF 6 need be preceded by the removal of PM having deposited in the PM sensor 8. This PM removal process is also referred to as "PM reset".

In the PM reset, the control unit 10 supplies a predetermined electric power to the heater of the PM sensor 8 so as to overheat and raise the temperature of the element part of the PM sensor 8. Thus, the PM adhered to the element part of the PM sensor 8 is combustively removed. It is assumed that the temperature for PM reset is higher than 500° C.

The PM reset may be performed at various timings. It is a general practice to perform the PM reset immediately after the start-up of the internal-combustion engine 2. After completion of the PM reset, the control unit is placed in a PM detection mode to perform the malfunction decision on the DPF 6.

Characteristic Control of the Embodiment

By the way, the exhaust gas contains Ash derived from a lubricant and metal compounds such as sulfate derived from oxidation of a catalyst as well as the PM including soot (soot-like particulate matter) and SOF (soluble organic fraction) which derive from combustion in the internal-combustion engine 2. In the following embodiments, only the components, such as soot and SOF, which are a detection object of the PM sensor 8 and derived from the combustion in the internal-combustion engine 2, will be defined as the "PM" as needed while the components such as Ash and metal compounds which are not derived from the combustion in the internal-combustion engine 2 will be defined as "poisonous substance" to be distinguished from the above.

The poisonous substances adhere to place between the electrodes 12, 14 of the PM sensor 8 together with the PM, affecting resistance value between the electrodes 12, 14. Therefore, in a case where the exhaust gas contains the poisonous substances, which adhere to the electrodes 12, 14, the adhered poisonous substances may induce variations in the sensor output, leading to an event that the sensor is incapable of exact detection of the PM amount.

Although the PM is combustively removed at PM reset temperature, much of the poisonous substances cannot be combusted, remaining adhered between the electrodes 12, 14. If the PM reset is repeated, therefore, the poisonous substances remaining between the electrodes 12, 14 progressively accumulate so that the deviation of output from the PM sensor 8 progressively increases. Thus, the PM sensor 8 may progressively deteriorate.

In the above-described malfunction decision on the DPF 6, for example, the malfunction of the DPF 6 is determined by comparing the estimated deposition amount of PM as estimated based on the model of the internal-combustion engine 2 and the PM emission volume corresponding to the output from the PM sensor 8. Therefore, in a case where the output from the PM sensor 8 is deviated due to the adhered poisonous substances, it is possible that correct decision is not made on the malfunction of the DPF 6.

It is therefore desirable to reduce the amount of poisonous substances adhered to the electrodes 12, 14 of the PM sensor 8, so as to suppress the output variations of the PM sensor 8 caused by the poisonous substances. Hence, the following control is performed according to the first embodiment.

Characteristic Control of the Embodiment

According to the first embodiment, the PM reset is first performed by raising the temperature of the element part after completion of engine warm-up following the start-up of the internal-combustion engine 2. Subsequently, the malfunction decision on the DPF 6 is performed. A state where the PM is collected between the electrodes 12, 14 by applying the capturing voltage is maintained during a period (first period) between the completion of the malfunction decision on the DPF 6 and a first reference value Ref1 (reference output) reached by the output of the PM sensor 8. Thus, a poisoning prevention layer (particulate layer) as a PM layer is formed on the electrode surfaces 12, 14.

After the formation of the poisoning prevention layer, the application of capturing voltage is shut off and the temperature of the element part is maintained at about 300° C. till the shutdown of the internal-combustion engine 2. Namely, the state where the poisoning prevention layer is formed on the electrode surfaces 12, 14 is maintained as it is during a period between the first reference value Ref1 reached by the output of the PM sensor 8 and the shutdown of the internal-combustion engine 2 (second period). This poisoning prevention layer prevents the poisonous substances in the exhaust gas from directly adhering to the electrodes 12, 14.

Even though the application of the capturing voltage is shut off, the PM and poisonous substances are made to adhere between the electrodes 12, 14 by inertial force. If the poisonous substances adhere, however, a thin poisoning prevention layer made of the PM layer is previously formed between the electrodes 12, 14. Much of the poisonous substances deposited on this poisoning prevention layer is separated and scattered from the electrodes 12, 14 by the combustion of the underlying PM layer when the PM reset is performed. Hence, the amount of poisonous substances remaining on the electrodes 12, 14 after the PM reset can be reduced.

Further, there is a potential of element fracture caused by heat stress if the temperature of the element part is raised immediately after the start-up of the internal-combustion engine 2 when the exhaust gas is at low temperature. It is therefore a general practice to perform the PM reset after the internal-combustion engine 2 is fully warmed up. However, the poisoning prevention layer formed of the PM has a water repellent effect. Hence, droplet contact area of the element part can be reduced to reduce the heat stress induced by temperature rise. If the PM reset is started shortly after the start-up of the internal-combustion engine 2, the element fracture can be prevented so that the control unit can enter the PM detection mode promptly.

Specific Control Routine of the Embodiment

Figure 3:
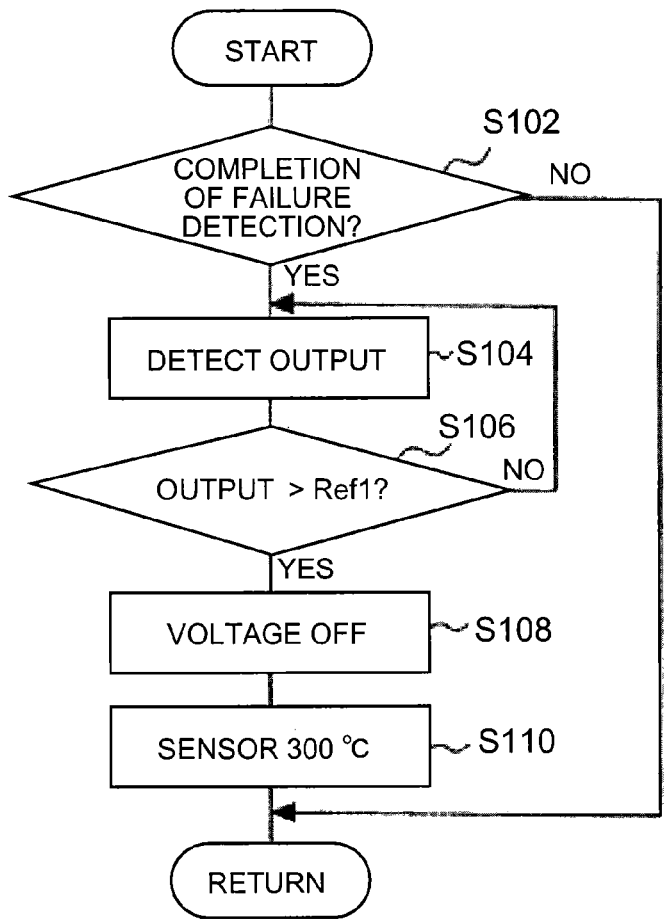
FIG. 3 is a flow chart showing the steps of a control routine executed by a control unit according to the first embodiment of the invention.

FIG. 3 is a flow chart showing the steps of a control routine executed by the control unit according to the embodiment of the invention. The routine of FIG. 3 is a routine executed at intervals of a given time period during the operation of the internal-combustion engine. In the routine of FIG. 3, whether the malfunction detection of DPF 6 is completed or not is first determined (S102). In this routine, the start-up of the internal-combustion engine 2 is followed by the malfunction detection of DPF 6. "YES" is given only when the first decision process after completion of the malfunction detection is performed. It is assumed here that the malfunction detection is performed once in one operation from start-up to shutdown of the internal-combustion engine 2. When an initiation condition of the malfunction detection of DPF 6 is satisfied, the malfunction of the DPF 6 is detected by comparing the estimated amount of PM emitted to the downstream of the DPF 6 and the estimated PM emission volume based on the output of the PM sensor 8. Aside from this routine, however, the malfunction detection of DPF 6 is performed according to a control program stored in the control unit 10.

If it is not determined in Step S102 that the malfunction detection of DPF 6 is completed, this processing is terminated. On the other hand, if it is determined in Step S102 that the malfunction detection of DPF 6 is completed, the subsequent step is performed to detect an output of the PM sensor 8 (S104). Next, whether or not the sensor output is smaller than the first reference value Ref1 (reference output) is determined (S106). The first reference value Ref1 means a value which is set based on an output provided when an amount of PM equivalent to the poisoning prevention layer is deposited on the electrodes 12, 14 and is stored in the control unit 10.

If "sensor output>first reference value Ref1" is not established in Step S106, Steps S104 to S106 to detect the sensor output and to determine whether or not "sensor output>first reference value Ref1" is established are repeated. On the other hand, if "sensor output>first reference value Ref1" is established in Step S106, it is determined that a predetermined amount of PM is deposited on the electrodes 12, 14 to form the poisoning prevention layer thereon. In this case, the subsequent step is performed to turn off the capturing voltage (Step S108). Thus, electrostatic collection of PM in the PM sensor 8 is terminated. The state where the thin poisoning prevention layer is formed on the electrodes 12, 14 is maintained as it is by turning off the power supply and hence, the direct adhesion of the poisonous substances onto the electrode surfaces 12, 14 can be prevented.

Subsequently, the sensor temperature is maintained at about 300° C. (Step S110). Thus is prevented the adhesion of the PM and poisonous substances to the element part. By maintaining the sensor at such high temperatures, the warm-up of the PM sensor 8 can be promptly completed at the subsequent engine start, permitting the system to enter the PM detection mode. Thereafter, the present process is terminated in this state.

According to the first embodiment, as described above, the direct adhesion of the poisonous substances onto the electrodes 12, 14 can be prevented by turning off the capturing voltage in the state where the poisoning prevention layer is formed. Since the poisoning prevention layer is formed, even the poisonous substances deposited thereon can be separated and scattered in conjunction with the combustion of the poisoning prevention layer in the execution of the PM reset.

Figure 4:
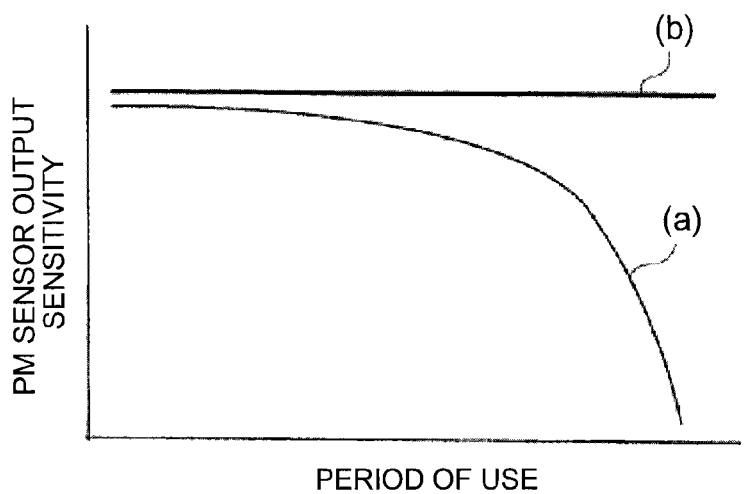
FIG. 4 is a graph illustrating an effect of the control according to the first embodiment of the invention.

FIG. 4 is a graph illustrating the difference in the variation of output sensitivity against the period of use by comparing the PM sensor 8 of the first embodiment and a conventional PM sensor. In FIG. 4, the period of use is plotted on the abscissa and the output sensitivity on the ordinate. Further in FIG. 4, a curve (a) represents the variation of output sensitivity of the conventional sensor while a curve (b) represents the variation of output sensitivity of the PM sensor 8 to which the control of the first embodiment is applied. As indicated by the curve (a) in FIG. 4, the conventional PM sensor is decreased in the output sensitivity with increase in the length of period of use due to the deposition of the poisonous substances. As indicated by the curve (b) in FIG. 4, on the other hand, the PM sensor 8 of the first embodiment is decreased in the poisonous-substance deposition between the electrodes 12, 14 and hence, can maintain high output sensitivity even though the period of use is extended.

According to the first embodiment, a period between the completion of malfunction detection of the DPF 6 and the first reference value Ref1 reached by the sensor output, for example, is equivalent to the "first period" of the invention. "Forming means" of the invention is implemented by applying the capturing voltage during this first period. Further according to the first embodiment, a period between the first reference value Ref1 reached by the sensor output and the shutdown of the internal-combustion engine 2, for example, is equivalent to the "second period" of the invention. "Maintaining means" of the invention is implemented by disabling the application of the capturing voltage (S108) during this second period. Further, "temperature control means" of the invention is implemented by maintaining the element temperature at about 300° C. (S110).

According to the invention, however, the "first period" during which the capturing voltage is applied for forming the poisoning prevention layer is not limited to this. For example, the "first period" may be defined by a period of a given length of time after the completion of malfunction detection of the DPF 6 and the poisoning prevention layer may be formed by applying the capturing voltage during this period. The same also holds for the following embodiments.

Further according to the invention, the "second period" during which the state where the poisoning prevention layer is formed is maintained is not limited to the period up to the shutdown of the internal-combustion engine 2. In a case where the malfunction detection of DPF 6 is performed multiple times during one operation from the start-up to the shutdown of the internal-combustion engine 2, for example, the "second period" may be defined by a period between the completion of the present malfunction detection of DPF 6 followed by the formation of the poisoning prevention layer and the start of the next malfunction detection of DPF 6. The same also holds for the following embodiments.

The first embodiment illustrates the case where the element temperature is maintained at about 300° C. after the formation of the poisoning prevention layer (S110), but the invention is not limited to this. Such a temperature control may be dispensed with. Even in the case where such a control of element temperature is provided, the temperature at which the element part is maintained is not limited to 300° C. However, it is preferred that the temperature at which the element part is maintained is lower than a PM reset temperature (500° C. in this embodiment) but is high enough to suppress the PM deposition on the element part. The same also holds for the following embodiments.

The first embodiment illustrates the malfunction detection of DPF 6 performed by comparing the estimated deposition amount of PM and the PM deposition amount based on the output of the PM sensor 8. However, the method of malfunction detection of DPF 6 does not limit the invention in any way. The malfunction detection may be accomplished by any other method. The same also holds for the following embodiments.

The first embodiment illustrates the case where the current value is detected as the output of the PM sensor 8, but the output of the PM sensor 8 according to the invention is not limited to this. The output may be a resistance value across the electrodes 12, 14 or any other electric characteristic correlated with the resistance value. The same also holds for the following embodiments.

Second Embodiment

A system and a PM sensor according to a second embodiment have the same configurations as those shown in FIG. 1 and FIG. 2. Instead of providing the control to form the poisoning prevention layer on and between the electrodes 12, 14 after the malfunction detection of DPF 6, the system of the second embodiment predicts time when the PM emission volume increases and performs control to permit the formation of the poisoning prevention layer at such a time.

In the regeneration of DPF 6, as described above, the PM deposited in the DPF 6 is combustively removed by raising the exhaust gas temperature. It is therefore expected that the amount of PM and poisonous substances emitted to the downstream of the DPF 6 increases during this process. Hence, it is desirable to prevent the adhesion of the PM and the like between the electrodes 12, 14 during this process.

In the system according to the second embodiment, therefore, the poisoning prevention layer is formed by depositing the PM on the electrode surfaces 12, 14 before the start of control to recover the DPF 6, thus protecting the electrodes 12, 14 during the regeneration control of DPF 6.

More specifically, the regeneration of DPF 6 according to the second embodiment is performed when the estimated deposition amount of PM, as estimated according to the model, reaches or exceeds a reference value (referred to as "second reference value Ref2" herein). According to the second embodiment, therefore, the start of the regeneration control of DPF 6 is predicted when the estimated deposition amount of PM in the DPF 6 reaches a third reference value Ref3 which is smaller than the second reference value Ref2. When the start of the regeneration control of DPF 6 is predicted, the PM reset is inhibited. At this time, the electrodes 12, 14 are subject to the capturing voltage. Hence, the PM is assuredly collected on the electrodes 12, 14 by inhibiting the PM reset.

During a period between the third reference value Ref3 reached by the estimated deposition amount of PM in the DPF 6 and the second reference value Ref2 reached by the estimated deposition amount of PM in the DPF 6 (first period), the state of applying the capturing voltage is established to collect the PM to form the poisoning prevention layer on the electrode surfaces 12, 14. The third reference value Ref3 for prediction of the start of the regeneration control of DPF 6 is set to a value such as to allow a necessary and adequate amount of PM deposition on the electrodes 12, 14 of the PM sensor 8 during the period between the third reference value Ref3 reached by the estimated deposition amount of PM and the second reference value Ref2 reached by the estimated deposition amount of PM. This value is previously obtained through experiments and the like and set arbitrarily.

Just after the regeneration of DPF 6, the DPF 6 is removed of the deposited PM. Hence, the DPF 6 is prone to facilitate the passage of the PM and tends to be decreased in purification performance. That is, the amount of PM and poisonous substances emitted to the exhaust gas downstream of the DPF 6 tends to increase just after the regeneration of DPF 6.

Therefore, the second embodiment also inhibits the PM reset for a given period of time just after the regeneration of DPF 6. Namely, even after the completion of the regeneration of DPF 6, the PM reset is inhibited until after the estimated deposition amount of PM in the DPF 6 reaches a fourth reference value Ref4 which is even smaller than the third reference value Ref3.

As described above, the PM reset is inhibited during a period between the third reference value Ref3 reached by the estimated deposition amount of PM followed by the prediction of the start of the regeneration of DPF 6 and the fourth reference value Ref4 reached by the estimated deposition amount of PM after the regeneration of DPF 6 (second period). Thus, the poisoning prevention layer is maintained to protect the electrode surfaces 12, 14 during and after the regeneration of DPF 6. This ensures that the direct adhesion of the poisonous substances onto the electrodes 12, 14 is prevented even in a region that allows a large amount of poisonous substances to flow out. It is noted that the fourth reference value Ref4 means a PM deposition amount required for maintaining high purification performance of the DPF 6 to some degree. The fourth reference value Ref4 is set to an optimum value through experiments and the like and previously stored in the control unit 10.

Figure 5:
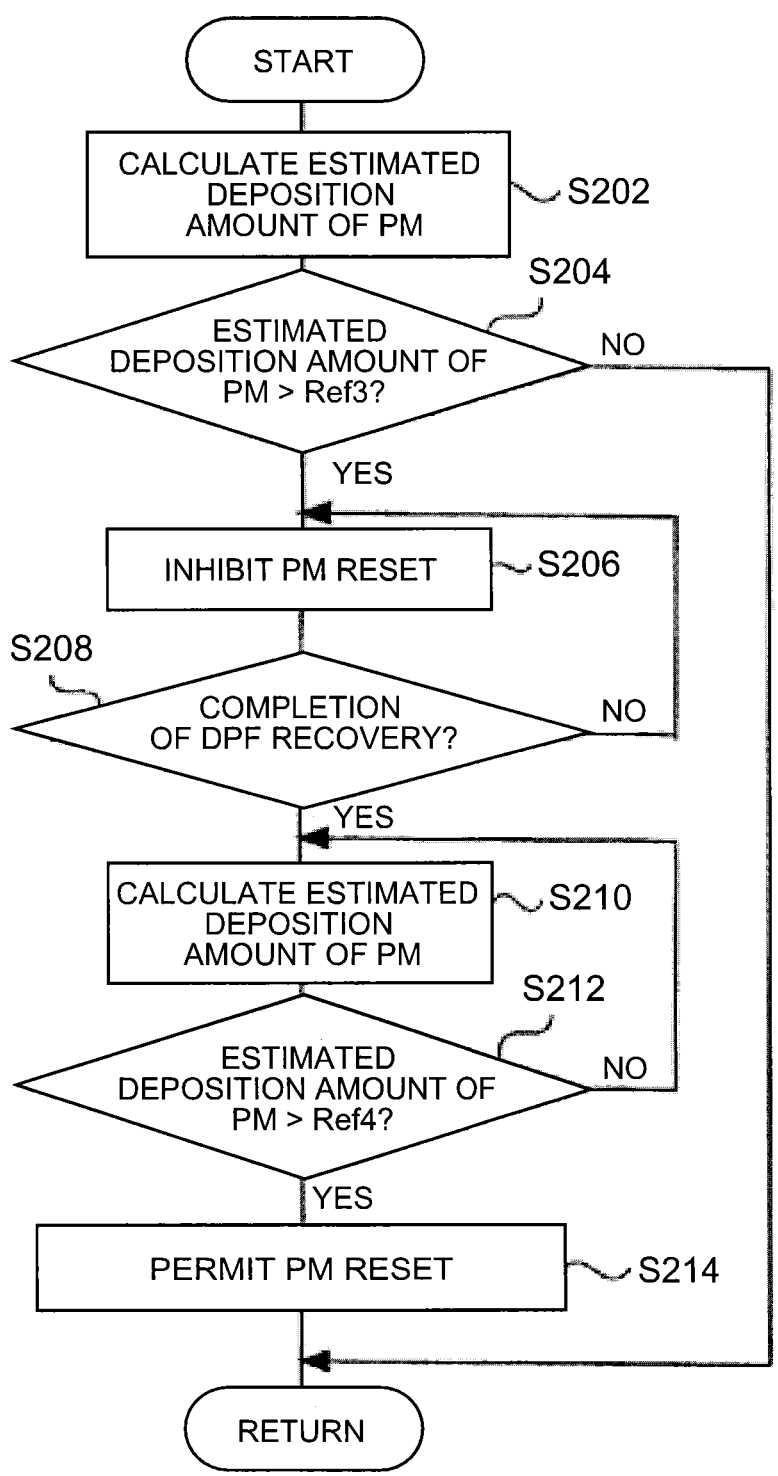
FIG. 5 is a flow chart showing the steps of a control routine executed by a control unit according to a second embodiment of the invention.

FIG. 5 is a flow chart showing the steps of a control routine executed by a control unit according to the second embodiment of the invention. This routine is repeated during the operation of the internal-combustion engine 2. In the routine of FIG. 5, the estimated deposition amount of PM in the DPF 6 is first calculated (S202). The estimated deposition amount of PM is calculated based on a model previously stored in the control unit 10.

Next, whether the value of the estimated deposition amount of PM is greater than the third reference value Ref3 or not is determined (S204). The third reference value Ref3 is a value based on which the regeneration of DPF 6 is predicted, and is previously stored in the control unit 10. If "estimated deposition amount of PM>third reference value Ref3" is not established in Step S204, the present processing is terminated here.

If "estimated deposition amount of PM>third reference value Ref3" is established in Step S204, on the other hand, the PM reset is inhibited (S206). Namely, the processing of removing the PM deposited in the PM sensor 8 is inhibited while the PM is continuously collected in the PM sensor 8 so that the poisoning prevention layer is formed and maintained.

Subsequently when the estimated deposition amount of PM reaches the second reference value Ref2, the regeneration of DPF 6 is performed. This processing of recovering the DPF 6 is executed according to a control program for the processing of regeneration of DPF 6 which is defined independently from the routine of FIG. 5 and stored in the control unit 10.

In the routine of FIG. 5, whether the regeneration of DPF 6 is completed or not is determined (S208). If it is not determined in Step S208 that the regeneration of DPF 6 is completed, the determination processing of Step S208 with the PM reset inhibited (S206) is repeated till it is determined that the regeneration of DPF 6 is completed.

On the other hand, if it is determined in Step S208 that the regeneration of DPF 6 is completed, the subsequent step is performed to calculate again the estimated deposition amount of PM in the DPF 6 (S210). The estimated deposition amount of PM calculated in this step is an estimated deposition amount after completion of the regeneration of DPF 6 and is calculated according to the model stored in the control unit 10 the same way as in Step S202.

Next, whether the estimated deposition amount of PM calculated in Step S210 is greater than the fourth reference value Ref4 or not is determined (S212). The fourth reference value Ref4 means a reference value which is used to determine whether or not a sufficient amount of PM for maintaining high purification performance of the DPF 6 to some degree is deposited in the DPF 6 and is previously stored in the control unit 10. If "estimated deposition amount of PM>fourth reference value Ref4" is not established in Step S210, the calculation of the estimated deposition amount of PM in Step S210 and the decision processing in Step S212 are repeated till this relation is established.

If "estimated deposition amount of PM>fourth reference value Ref4" is established in Step S210, on the other hand, it is determined that the DPF 6 is increased in the purification performance so that the amount of PM emitted to the downstream of the DPF 6 is decreased. In this case, therefore, the inhibition of PM reset is cancelled (S214). When this state is established, the PM reset is performed at a necessary timing and according to another control program stored in the control unit 10.

According to the second embodiment, as described above, the timing of the regeneration of DPF 6 is predicted so as to inhibit the PM reset before the start of the regeneration and subsequently, the PM reset is inhibited during a period between the completion of the regeneration of DPF 6 and the re-deposition of a given amount of PM in the DPF 6. It is noted here that the amount of PM emitted to the downstream of the DPF 6 is expected to increase both during the regeneration of DPF 6 and during a given period of time just after the regeneration of DPF 6. In this regard, the second embodiment is adapted to predict the period of the increase of PM amount and to allow the poisoning prevention layer to be previously formed on the electrode surfaces 12, 14 of the PM sensor 8. Thus, the electrodes 12, 14 are protected by the poisoning prevention layer during the period when the PM amount in the exhaust gas is high and the electrodes 12, 14 are susceptible to the deposition of the poisonous substances. Accordingly, the direct adhesion of the poisonous substances onto the electrodes 12, 14 is effectively suppressed so that the deterioration of the PM sensor 8 is suppressed. Hence, the PM sensor can maintain the high output sensitivity.

According to the second embodiment, the period between the prediction of the DPF regeneration and the start of the DPF regeneration is equivalent to the "first period" of the invention. The "forming means" of the invention is implemented by establishing the state of applying the capturing voltage during this period. According to the second embodiment, the period between the prediction of the regeneration of DPF 6 followed by the completion of the regeneration control of DPF 6 and the fourth reference value Ref4 reached by the estimated deposition amount of PM is equivalent to the "second period" of the invention. The "maintaining means" of the invention is implemented by inhibiting the PM reset during this period.

The second embodiment illustrates the case where the PM reset is inhibited with attention focused on the period of the regeneration of DPF 6 and the period just after the regeneration of DPF 6 as the region where the amount of PM in the exhaust gas downstream from the DPF 6 is apt to increase. However, the "second period" of the invention in which the PM reset is inhibited is not limited to this. For example, the "second period" may be a period up to the completion of regeneration of DPF 6 and the poisoning prevention layer may be maintained by inhibiting the PM reset only during this period. Alternatively, the "second period" may be defined only by, for example, a period between the completion of DPF regeneration and the fourth reference value reached by the estimated deposition amount of PM and the PM reset may be inhibited only during this period. The same also holds for the following embodiments.

Further, the invention is not applied only to the time of the regeneration of DPF 6 and the time just after the regeneration of DPF 6 but can also be applied to, for example, an operation region where the other poisonous substances are apt to increase. Specifically, the poisonous substances are thought to be apt to increase during the control of NSC sulfur poisoning prevention or during the control of NOx reduction, for example. Hence, the deposition of the poisonous substances on the electrode surfaces 12, 14 can be suppressed by predicting the start of these controls; forming the poisoning prevention layer on the PM sensor during the "first period" prior to the execution of these controls; and maintaining the poisoning prevention layer by inhibiting the PM reset during the "second period" in which these controls are performed. The same also holds for the following embodiments.

The invention is not limited to the control flow of predicting the start of a certain control and inhibiting the PM reset. For example, a control sequence may be contemplated which includes: predicting a timing of shutting down the internal-combustion engine 2 based on navigation information; and inhibiting the PM reset shortly before the engine shutdown. This provides a state where the poisoning prevention layer is formed at the subsequent engine start. Since the poisoning prevention layer has a water repellent effect, the poisoning prevention layer may be formed at the time of engine shutdown whereby the PM sensor 8 is promptly made available while preventing the element fracture at the start-up of the internal-combustion engine 2. The same also holds for the following embodiments.

The second embodiment illustrates the case where when the third reference value Ref3 is reached by the estimated deposition amount of PM in the DPF 6, the PM reset is simply inhibited so as to allow a given amount of PM to be deposited to form the poisoning prevention layer during the period up to the regeneration of DPF 6. However, the invention is not limited to this. A control may be provided such as to form the poisoning prevention layer actively. Specifically, in a case where time to the start of the regeneration of DPF 6 or to the start of control for catalyst poisoning prevention is short, control may be provided such that the shorter the time, the higher the capturing voltage applied. This permits the PM to be more quickly deposited on the electrodes 12, 14 to form the poisoning prevention layer thereon. However, the application of an excessively high voltage may result in insulation breakdown of the element part, short-circuited electrodes 12, 14 or the like. Therefore, the voltage to be applied need be set within such a range as not to induce the above problems. The same also holds for the following embodiments.

Third Embodiment

A system and a PM sensor according to a third embodiment have the same configurations as shown in FIG. 1 and FIG. 2. The third embodiment performs control combining the controls of the first and second embodiments.

Figure 6:
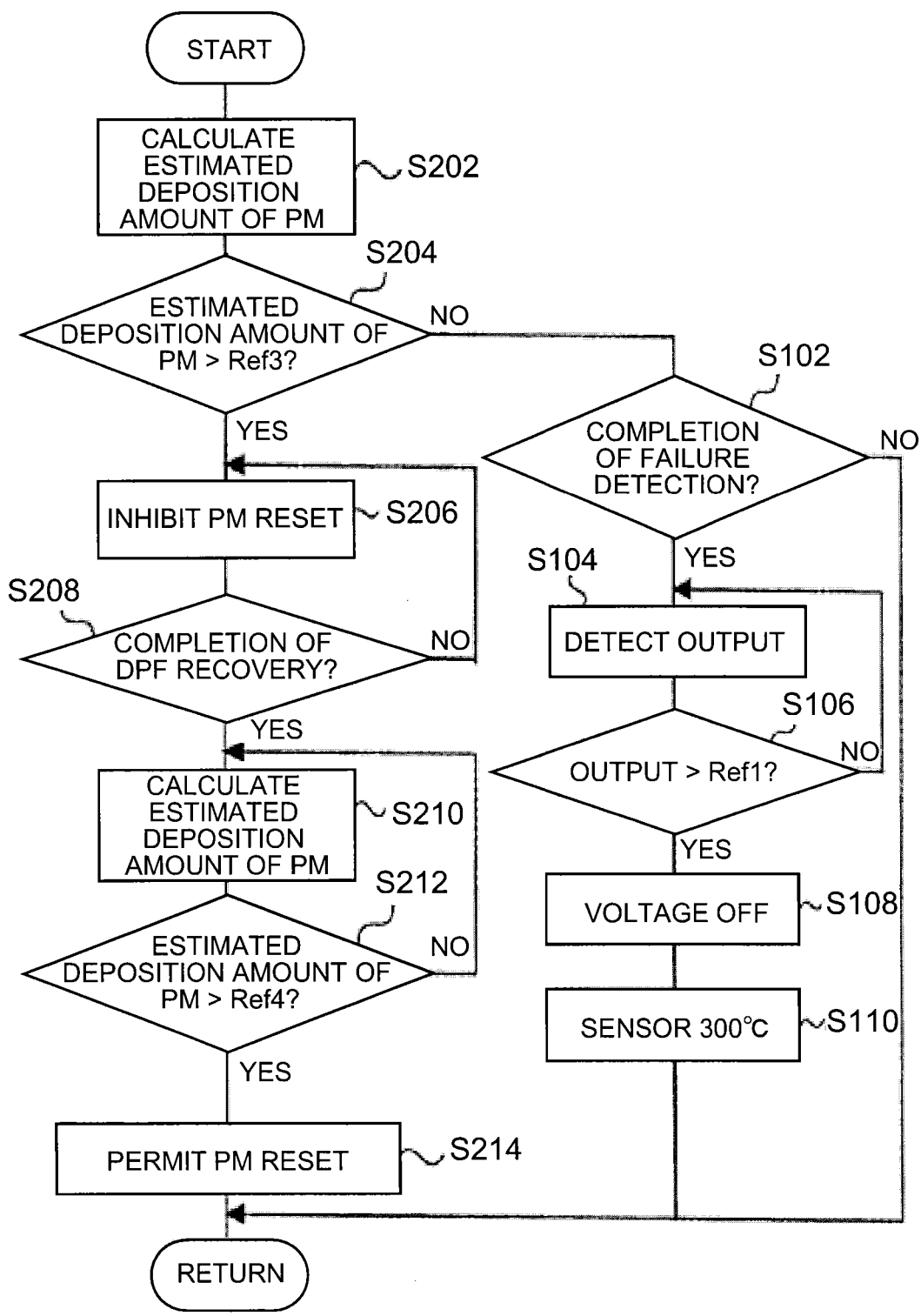
FIG. 6 is a flow chart showing the steps of a control routine executed by a control unit according to a third embodiment of the invention.

FIG. 6 is a flow chart showing the steps of a control executed by a control unit 10 according to the third embodiment of the invention. In a routine of FIG. 6, the same steps as S202 to S214 shown in FIG. 5 of the second embodiment are first performed. Namely, whether the regeneration of DPF 6 is predicted or not is determined (S202, S204). If the regeneration of DPF 6 is predicted, the PM reset is inhibited (S206). Subsequently, the inhibition of PM reset is continued during the period between the completion of the regeneration of DPF 6 (S208) and the determination of the deposition of a given amount of PM in the DPF 6 (S210, S212). When the deposition of a given amount of PM is determined, the PM reset is permitted (S214). Subsequently, the present processing is terminated.

However, if "estimated deposition amount of PM>third reference value Ref3" is not established in Step S204, the same steps as S102 to S110 shown in FIG. 3 of the first embodiment are started subsequently. Specifically, whether the malfunction detection of DPF 6 is completed or not is determined in Step S102. If the malfunction detection is not completed, the present processing is terminated in this embodiment.

On the other hand, if it is determined in Step S102 that the malfunction detection is completed, whether the detected sensor output (S104) is greater than the first reference value Ref1 or not is determined (S106). This determination step is repeated till "sensor output>first reference value Ref1" is established, whereby the poisoning prevention layer is formed on the surface of the PM sensor 8. Subsequently, the application of the capturing voltage is shut off (S108) and the element part of the PM sensor 8 is maintained at about 300° C. (S110). Subsequently, the present processing is terminated.

Fourth Embodiment

A system and a PM sensor 8 according to a fourth embodiment have the same configurations as those shown in FIG. 1 and FIG. 2. The fourth embodiment performs the same control as that of the third embodiment except that the control of the third embodiment is performed only when the volume of PM emission from the internal-combustion engine 2 is greater than a predetermined value. That is, in the system of the fourth embodiment, the normal PM detection mode is given priority in the region where the volume of PM emission from the internal-combustion engine 2 is expected to be low.

Specifically, the PM amount in the exhaust gas emitted from the internal-combustion engine 2 is estimated from a combustion model of the internal-combustion engine 2. The control of FIG. 3 is performed or inhibited depending upon whether or not the estimated PM amount is greater than a fifth reference value Ref5 (reference emission volume). It is noted here that the fifth reference value Ref5 is set to a value in vicinity of an upper limit that provides a deposition amount of poisonous substances on the PM sensor 8 within an allowable range. This value is obtained through experiments and the like and in consideration of the PM sensor and the allowable range of deposition amount, and is stored in the control unit 10.

Figure 7:
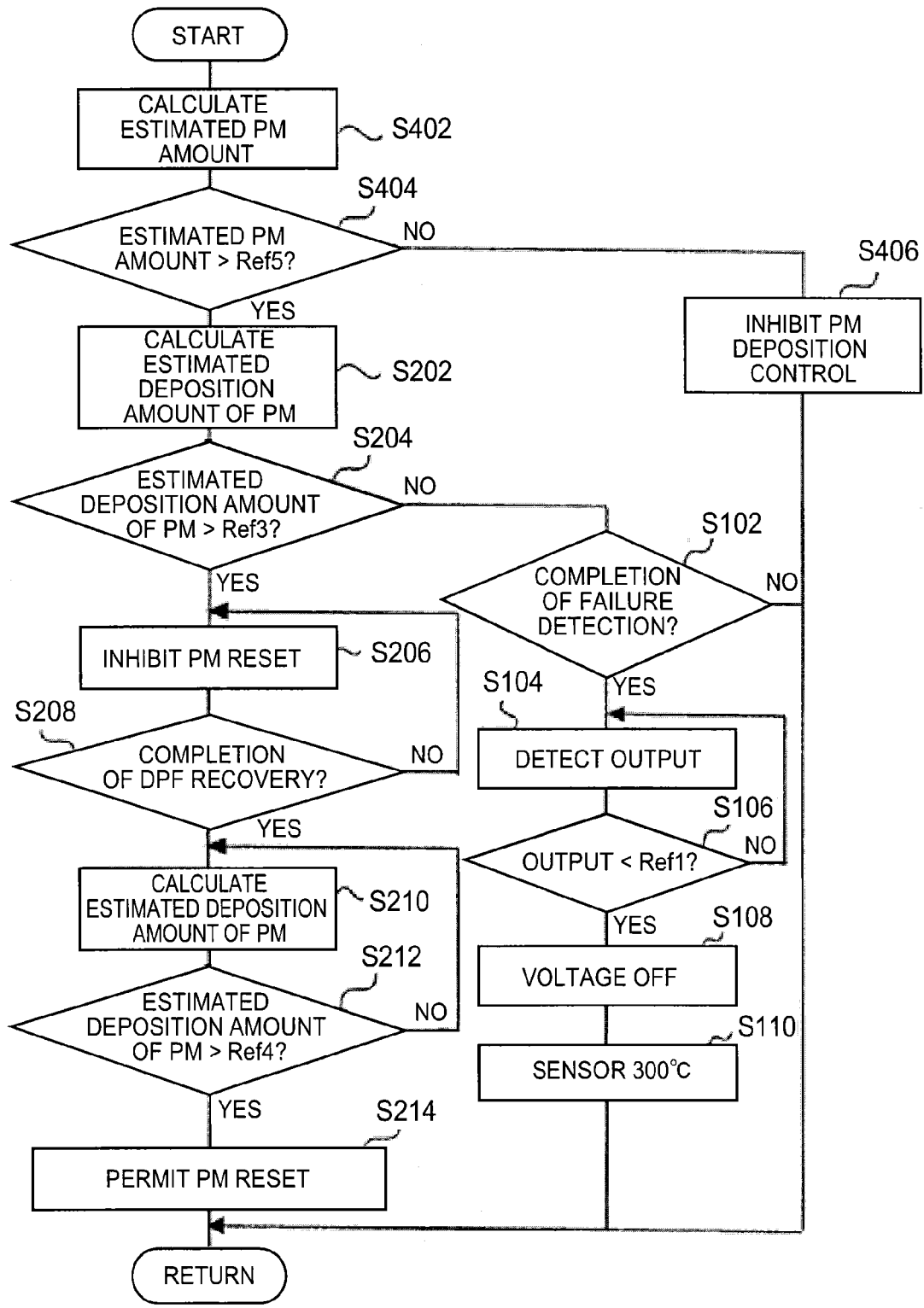
FIG. 7 is a flow chart showing the steps of a control routine executed by a control unit according to a fourth embodiment of the invention.

FIG. 7 is a flow chart showing the steps of a control routine executed by a control unit according to the fourth embodiment of the invention. The routine of FIG. 7 is the same as the routine of FIG. 6 except that the routine of FIG. 7 further includes Steps S402 to S406. Specifically, the estimated PM amount is first calculated in the routine of FIG. 7 (S402). The estimated PM amount is the amount of PM in the exhaust gas emitted from the internal-combustion engine 2 and is calculated according to a model or the like.

Next, whether the estimated PM amount is greater than the fifth reference value Ref5 or not is determined (S404). If "estimated PM amount>fifth reference value Ref5" is not established here, the PM deposition control for forming the poisoning prevention layer illustrated in FIG. 6 is inhibited (S406) and the present processing is terminated. On the other hand, if "estimated PM amount>fifth reference value Ref5" is established in Step S404, the same steps as those of FIG. 6 follow and the present processing is terminated.

According to the fourth embodiment, as described above, the formation of the poisoning prevention layer is inhibited in the region where the estimated PM amount is low, and the sensor is used as the normal PM sensor. On the other hand, the control to form the poisoning prevention layer is performed in the region where the estimated PM amount is high. In this manner, the poisoning prevention layer is formed as needed to protect the electrodes 12, 14 while the PM sensor output can be obtained from the PM sensor 8 without the poisoning prevention layer formed thereon in the region where the PM amount is low. Thus, the PM sensor 8 is effectively improved in durability while the detection of PM amount and the malfunction detection can be accomplished with higher accuracies in the region where the PM emission volume is low.

The fourth embodiment illustrates the case where the PM deposition control is inhibited when the estimated PM amount is calculated and the estimated PM amount thus calculated is equal to or less than the fifth reference value. According to the invention, however, the basis of the decision on the inhibition of the PM deposition control is not limited to the comparison between the estimated PM amount and the fifth reference value.

Further, the fourth embodiment illustrates the case where the invention is applied to the third embodiment but the processing of FIG. 6 is inhibited in the region where the estimated PM amount is low. However, the invention is not limited to this and the control of the fourth embodiment is applicable to the control to form the poisoning prevention layer and to maintain the same as illustrated by the first embodiment or the second embodiment.

The number, numerical quantity, volume, range or the like of each of the elements stated in the above embodiments does not limit the invention unless such number, numerical quantity, volume, range or the like is particularly defined or clearly specified in principle. The configurations, steps and the like illustrated by the embodiments are not necessarily essential to the invention unless such a configuration, step or the like is particularly defined or clearly specified in principle.

DESCRIPTION OF REFERENCE NUMERALS

2: internal-combustion engine
4: exhaust passage
6: DPF
8: PM sensor
10: control unit

The invention claimed is:
1. A control device for an internal-combustion engine, the control device comprising:
    a particulate matter sensor installed in an exhaust passage of the internal-combustion engine;
    a particulate capturing filter configured to capture particulate matter contained in an exhaust gas and disposed in the exhaust passage at place upstream of the particulate matter sensor;
    an electronic control unit configured to detect a particulate amount in the exhaust gas through the exhaust passage in response to an output from the particulate matter sensor;
    the electronic control unit configured to apply a particulate capturing voltage between electrodes of the particulate matter sensor during a first period so as to form a particulate layer on surfaces of the electrodes of the particulate matter sensor; and
    the electronic control unit configured to stop applying the particulate capturing voltage during a second period to maintain the particulate layer;
    the electronic control unit configured to execute a malfunction detection control to determine whether a malfunction of the particulate capturing filter exists or not, wherein the first period is a period between the completion of the malfunction detection control and a time when the output of the particulate matter sensor reaches a reference output, and the second period is a period between the time when the output of the particulate matter sensor reaches the reference output.

2. The control device according to claim 1, wherein the second period is a period between the time when the output of the particulate matter sensor reaches the reference output and a stoppage of the internal-combustion engine, in a case where the malfunction detection control is performed once during a period between the start-up and the stoppage of the internal-combustion engine.

3. The control device according to claim 1, wherein the second period is a period between the time when the output of the particulate matter sensor reaches the reference output and the start of a next malfunction detection control, in a case where the malfunction detection control is performed multiple times during the period between the start-up and a stoppage of the internal-combustion engine.

4. The control device according to claim 1, wherein the electronic control unit is configured to raise temperature of an element part formed with the electrodes of the particulate matter sensor to remove the particulate matter deposited on the element part; and the electronic control unit is configured to control the element part to be at a predetermined temperature during a period between voltage application continued until the output of the particulate matter sensor reaches the reference output and a stoppage of the internal-combustion engine, the predetermined temperature being lower than a temperature for combustive removal of the particulate matter and for suppressing deposition of the particulate matter on the element part.

5. A control device for an internal-combustion engine, the control device comprising:

a particulate matter sensor installed in an exhaust passage of an internal-combustion engine;

a particulate capturing filter configured to capture particulate matter contained in exhaust gas and disposed in the exhaust passage at place upstream of the particulate matter sensor;

an electronic control unit configured to detect a articulate amount in the exhaust gas through the exhaust passage in response to an output from the particulate matter sensor;

the electronic control unit configured to raise temperature of an element part formed with electrodes of the particulate matter sensor so as to combustively remove the particulate matter deposited on the element part, the electronic control unit configured to apply a particulate capturing voltage between the electrodes of the particulate matter sensor during a first period so as to form a particulate layer on surfaces of the electrodes of the particulate matter sensor, the first period including at least a period up to the start of filter regeneration control to remove the particulate matter deposited in the particulate capturing filter, and the electronic control unit configured to inhibit combustive removal of the particulate matter on the element part to maintain the formed particulate layer during a second period, the second period including at least a period between a prediction of the start of the filter regeneration control and completion of the filter regeneration control.

6. The control device according to claim 5, wherein the first period includes a period between the prediction of the start of the filter regeneration control and the start of the filter regeneration control.

7. The control device according to claim 5, wherein the second period further includes a period between the completion of the filter regeneration control and a time when an amount of particulate matter deposited in the particulate capturing filter exceeds a reference deposition amount.

8. The control device according to claim 1, wherein the electronic control unit is configured to estimate the particulate amount in the exhaust gas emitted from the internal-combustion engine; and the electronic control unit is configured to inhibit the maintaining of the particulate layer in a case where the estimated particulate amount is smaller than a reference emission volume.

9. The control device according to claim 5, wherein the electronic control unit is configured to estimate the particulate amount in the exhaust gas emitted from the internal-combustion engine; and the electronic control unit is configured to inhibit maintaining of the particulate layer in a case where the estimated particulate amount is smaller than a reference emission volume.

* * * * *